(12) United States Patent
Moehring et al.

(10) Patent No.: US 11,317,811 B2
(45) Date of Patent: May 3, 2022

(54) INFRARED OTOSCOPE FOR CHARACTERIZATION OF EFFUSION

(71) Applicant: OtoNexus Medical Technologies, Inc., Seattle, WA (US)

(72) Inventors: Mark A. Moehring, Seattle, WA (US); George A. Gates, Boerne, TX (US); Daniel Kreindler, Foster City, CA (US); Jay A. Chesavage, Palo Alto, CA (US)

(73) Assignee: OTONEXUS MEDICAL TECHNOLOGIES, INC., Seattle, WA (US)

( * ) Notice: Subject to any disclaimer, the term of this patent is extended or adjusted under 35 U.S.C. 154(b) by 110 days.

(21) Appl. No.: 16/438,603

(22) Filed: Jun. 12, 2019

(65) Prior Publication Data
US 2020/0029820 A1    Jan. 30, 2020

Related U.S. Application Data

(63) Continuation of application No. 15/609,015, filed on May 31, 2017, now Pat. No. 10,357,161.

(51) Int. Cl.
*A61B 5/00* (2006.01)
*A61B 1/227* (2006.01)
(Continued)

(52) U.S. Cl.
CPC ........ *A61B 5/0086* (2013.01); *A61B 1/00009* (2013.01); *A61B 1/00165* (2013.01);
(Continued)

(58) Field of Classification Search
CPC ....... A61B 5/0086; A61B 5/0066; A61B 5/12; A61B 5/14507; A61B 1/00009;
(Continued)

(56) References Cited

U.S. PATENT DOCUMENTS 5,115,133 A    5/1992 Knudson et al.
5,321,501 A    6/1994 Swanson et al.
(Continued)

FOREIGN PATENT DOCUMENTS

JP    2007500542 A    1/2007
JP    2014519393 A    8/2014
(Continued)

OTHER PUBLICATIONS

U.S. Appl. No. 16/043,584 Office Action dated Sep. 18, 2020.
(Continued)

*Primary Examiner* — Ellen C Hammond
*Assistant Examiner* — David C Comstock
(74) *Attorney, Agent, or Firm* — Wilson Sonsini Goodrich & Rosati

(57) ABSTRACT

An otoscope uses differential reflected response of optical energy at an absorption range and an adjacent wavelength range to determine the presence of water (where the wavelengths are water absorption wavelength and adjacent non-absorption excitation wavelengths). In another example of the invention, the otoscope utilizes OCT in combination with absorption and non-absorption range for bacteria and water.

22 Claims, 7 Drawing Sheets

(51) Int. Cl.
*G01B 9/02091* (2022.01)
*A61B 5/12* (2006.01)
*A61B 1/06* (2006.01)
*A61B 5/145* (2006.01)
*A61B 1/00* (2006.01)
*A61B 8/00* (2006.01)
*A61B 1/07* (2006.01)
*G01J 5/02* (2022.01)
*G01J 5/04* (2006.01)
*G02B 6/036* (2006.01)
*G02B 23/24* (2006.01)

(52) U.S. Cl.
CPC .......... *A61B 1/0638* (2013.01); *A61B 1/0669* (2013.01); *A61B 1/227* (2013.01); *A61B 5/0066* (2013.01); *A61B 5/12* (2013.01); *A61B 5/14507* (2013.01); *A61B 8/44* (2013.01); *G01B 9/02091* (2013.01); *A61B 1/0646* (2013.01); *A61B 1/07* (2013.01); *G01J 5/02* (2013.01); *G01J 5/04* (2013.01); *G02B 6/03694* (2013.01); *G02B 23/24* (2013.01)

(58) Field of Classification Search
CPC . A61B 1/00165; A61B 1/0638; A61B 1/0669; A61B 1/227; A61B 1/0646; A61B 1/07; A61B 8/44; G01J 5/02; G01J 5/04; G02B 6/03694; G02B 23/24
USPC ....... 600/114, 160, 178, 180, 200, 476, 477, 600/478
See application file for complete search history.

(56) References Cited

U.S. PATENT DOCUMENTS

| | | | |
|---|---|---|---|
| 5,383,467 A | 1/1995 | Auer et al. | |
| 6,950,692 B2 | 9/2005 | Gelikonov et al. | |
| 7,632,232 B2 | 12/2009 | Lewandowski et al. | |
| 7,751,057 B2 | 7/2010 | Oldenburg et al. | |
| 8,115,934 B2 | 2/2012 | Boppart et al. | |
| 8,594,757 B2 | 11/2013 | Boppart et al. | |
| 9,014,792 B2 | 4/2015 | Goldfain et al. | |
| 9,364,148 B2 | 6/2016 | Roberts | |
| 9,638,511 B2 | 5/2017 | Boppart et al. | |
| 9,788,712 B2 | 10/2017 | Seth et al. | |
| 9,867,528 B1 | 1/2018 | Boppart et al. | |
| 9,918,622 B2 | 3/2018 | Seth et al. | |
| 10,258,238 B2 | 4/2019 | Boppart et al. | |
| 10,278,570 B2 | 5/2019 | Shelton et al. | |
| 10,296,780 B2* | 5/2019 | Karygianni | G06K 9/6224 |
| 10,327,627 B2* | 6/2019 | Berkner | A61B 1/055 |
| 10,357,161 B1 | 7/2019 | Chesavage et al. | |
| 10,401,141 B2 | 9/2019 | Boppart et al. | |
| 10,568,515 B2 | 2/2020 | Moehring et al. | |
| 2002/0087084 A1* | 7/2002 | Shahar | A61B 5/0075 600/475 |
| 2003/0171655 A1 | 9/2003 | Newman et al. | |
| 2005/0059868 A1 | 3/2005 | Schurman | |
| 2006/0229509 A1 | 10/2006 | Al-Ali et al. | |
| 2006/0282009 A1 | 12/2006 | Oberg et al. | |
| 2007/0112273 A1 | 5/2007 | Rogers et al. | |
| 2007/0129632 A1 | 6/2007 | Voie et al. | |
| 2009/0037922 A1 | 2/2009 | Herington | |
| 2009/0185191 A1 | 7/2009 | Boppart et al. | |
| 2011/0286505 A1 | 11/2011 | Hedley et al. | |
| 2013/0023914 A1 | 1/2013 | Truong et al. | |
| 2013/0165763 A1 | 6/2013 | Huang et al. | |
| 2013/0289353 A1 | 10/2013 | Seth et al. | |
| 2013/0342826 A1 | 12/2013 | Goldfain et al. | |
| 2014/0206979 A1* | 7/2014 | Berkner | A61B 1/00186 600/407 |
| 2014/0249426 A1 | 9/2014 | Huh et al. | |
| 2014/0316278 A1 | 10/2014 | Addison et al. | |
| 2015/0169435 A1 | 6/2015 | Wu et al. | |
| 2015/0374208 A1 | 12/2015 | Ruppersberg et al. | |
| 2016/0007840 A1 | 1/2016 | Boppart et al. | |
| 2017/0014053 A1 | 1/2017 | Moehring et al. | |
| 2017/0049309 A1* | 2/2017 | Lepple-Wienhues | A61B 5/12 |
| 2017/0360302 A1 | 12/2017 | Chesavage et al. | |
| 2018/0242847 A1* | 8/2018 | Boppart | A61B 5/7257 |
| 2018/0256031 A1 | 9/2018 | Adamson et al. | |
| 2018/0303348 A1 | 10/2018 | Boppart et al. | |
| 2019/0142258 A1 | 5/2019 | Shelton et al. | |
| 2019/0320887 A1 | 10/2019 | Shelton et al. | |
| 2019/0343390 A1 | 11/2019 | Boppart et al. | |
| 2019/0368929 A1 | 12/2019 | Zhang et al. | |

FOREIGN PATENT DOCUMENTS

| | | |
|---|---|---|
| WO | WO-2015169435 A1 | 11/2015 |
| WO | WO-2016182999 A1 | 11/2016 |
| WO | WO-2017222947 A1 | 12/2017 |
| WO | WO-2018129430 A1 | 7/2018 |
| WO | WO-2018160561 A1 | 9/2018 |
| WO | WO-2018222782 | 12/2018 |
| WO | WO-2018222782 A1 | 12/2018 |

OTHER PUBLICATIONS

EP17815982.8 Extended Search Report dated Jan. 8, 2020.
PCT/us2018/035228 International Search Report dated Aug. 7, 2018.
U.S. Appl. No. 15/188,750 Notice of Allowance dated Nov. 13, 2019.
U.S. Appl. No. 15/609,015 Notice of Allowance dated Mar. 14, 2019.
U.S. Appl. No. 15/188,750 Office Action dated Mar. 7, 2019.
U.S. Appl. No. 15/609,015 Office Action dated Jul. 6, 2018.
"Office Action dated Jul. 6, 2018 for U.S. Appl. No. 15/609,015."
"PCT/US17/38052 International Search Report dated Oct. 24, 2017."
Co-pending U.S. Appl. No. 16/043,584, filed Jul. 24, 2018.
Sorrell et al., Bacteria Identification of Otitis Media with Fluorescence Spectroscopy, Lasers in Surgery and Medicine, 14:155-163 (1994).
Spector et al., Noninvasive Fluorescent Identification of Bacteria Causing Acute Otitis Media in a Chinchilla Model, The Laryngoscope, 110:1119-1123 (2000).
EP18808827.2 European Search Report dated Sep. 29, 2020.
Notice of Allowance dated Nov. 13, 2019 for U.S. Appl. No. 15/188,750.
Office action dated Mar. 7, 2019 for U.S. Appl. No. 15/188,750.
U.S. Appl. No. 16/043,584 Office Action dated Dec. 18, 2020.
U.S. Appl. No. 16/043,584 Office Action dated Jul. 14, 2021.
U.S. Appl. No. 16/043,584 Office Action dated Mar. 16, 2021.

* cited by examiner

IR Spectroscopy system

IR Speculum Tip detail

Normalized spectral response from TM

Measurement waveforms

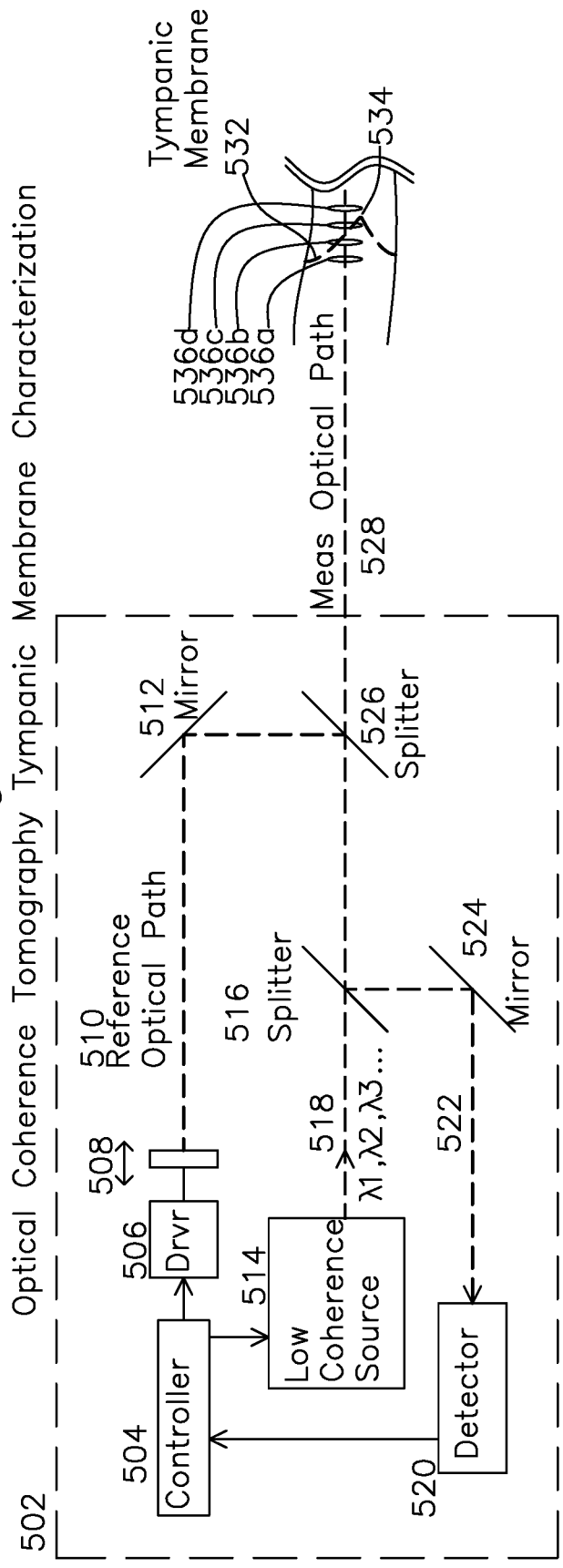
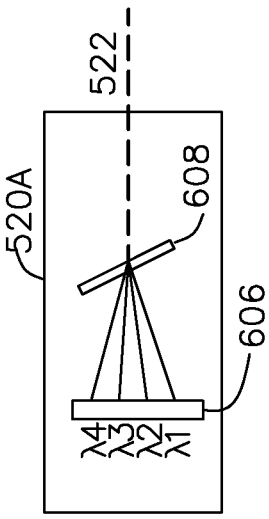
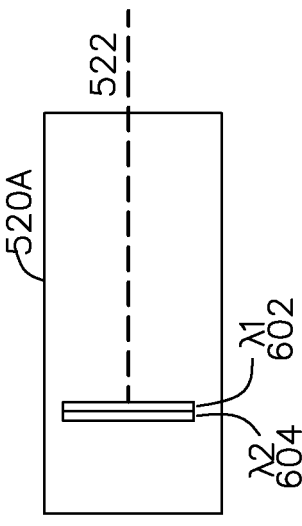

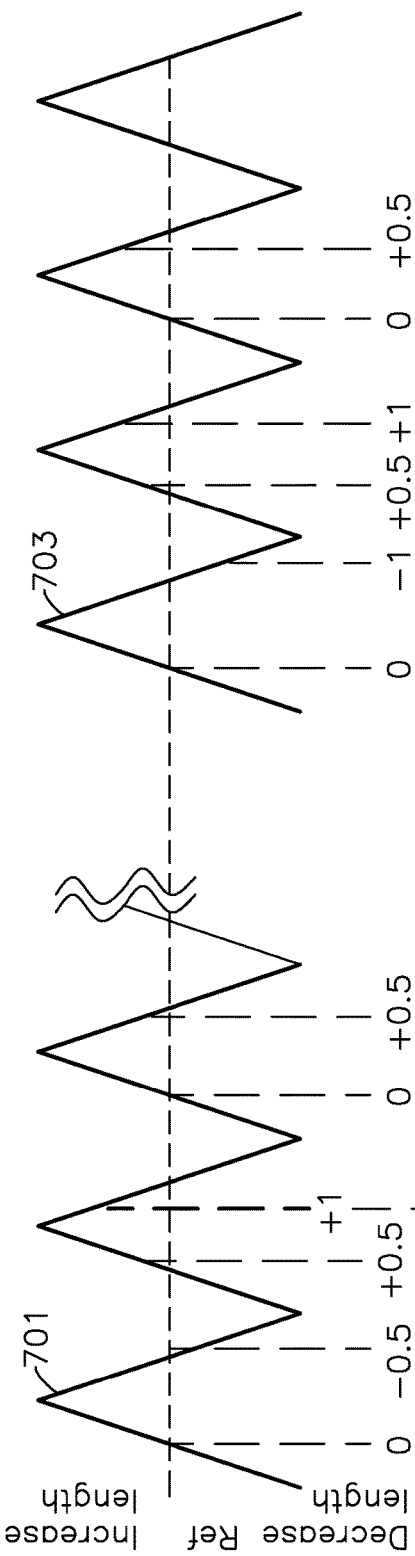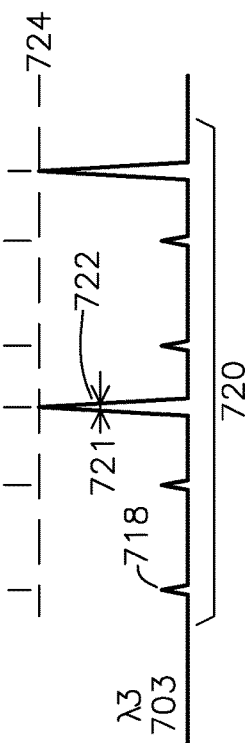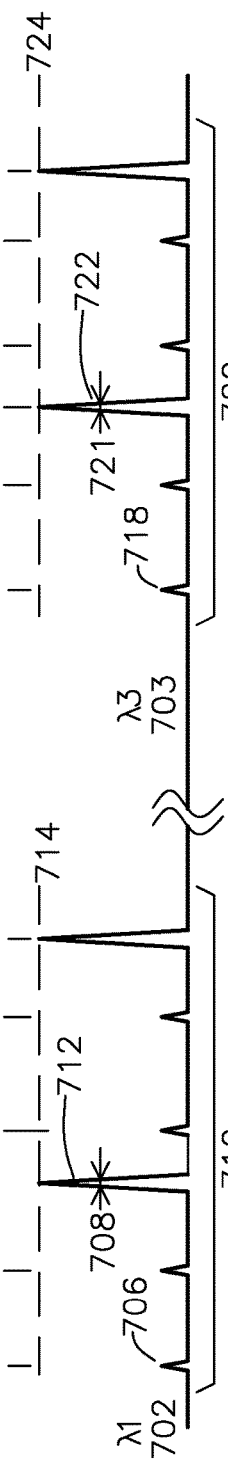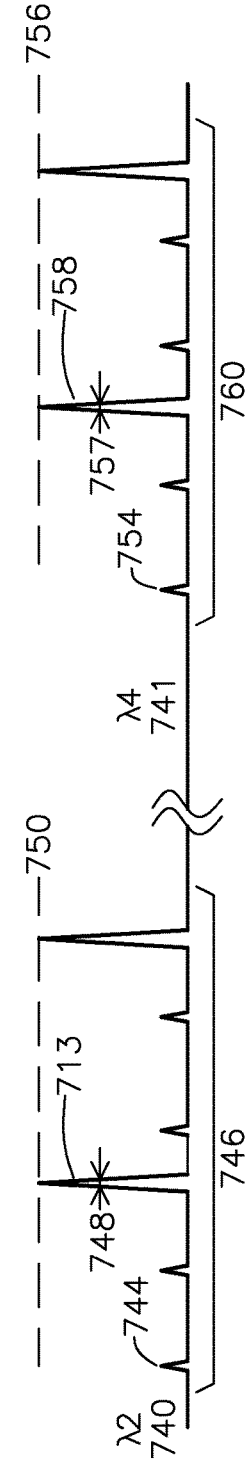

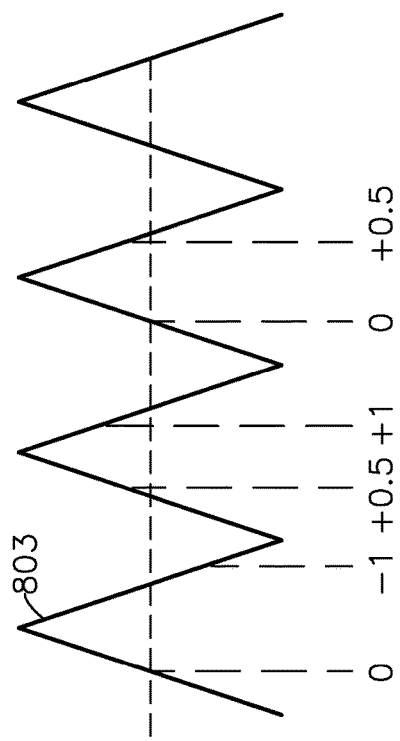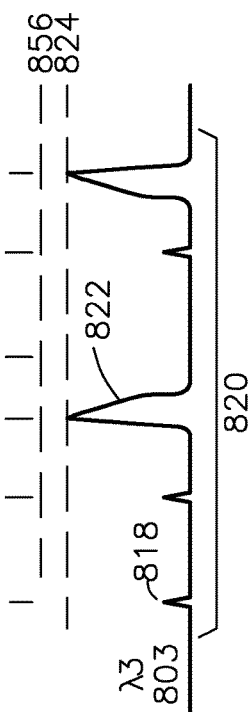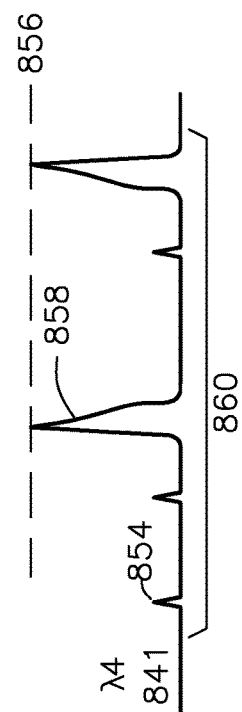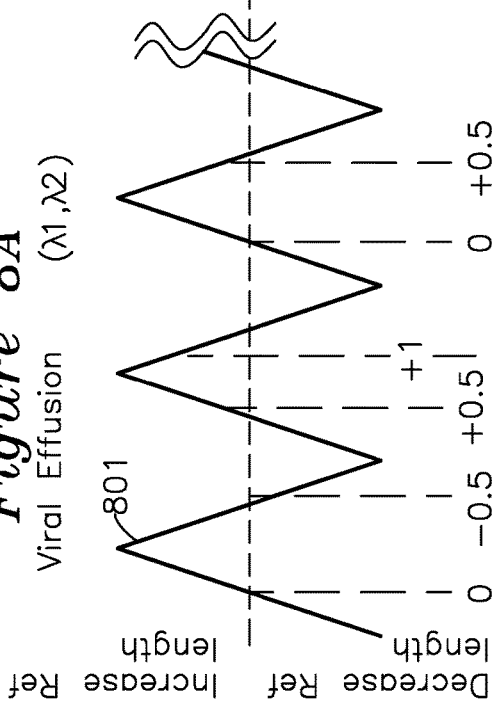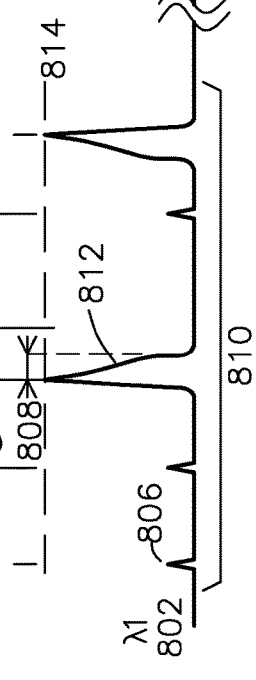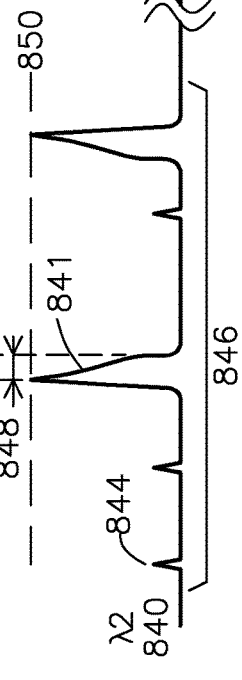

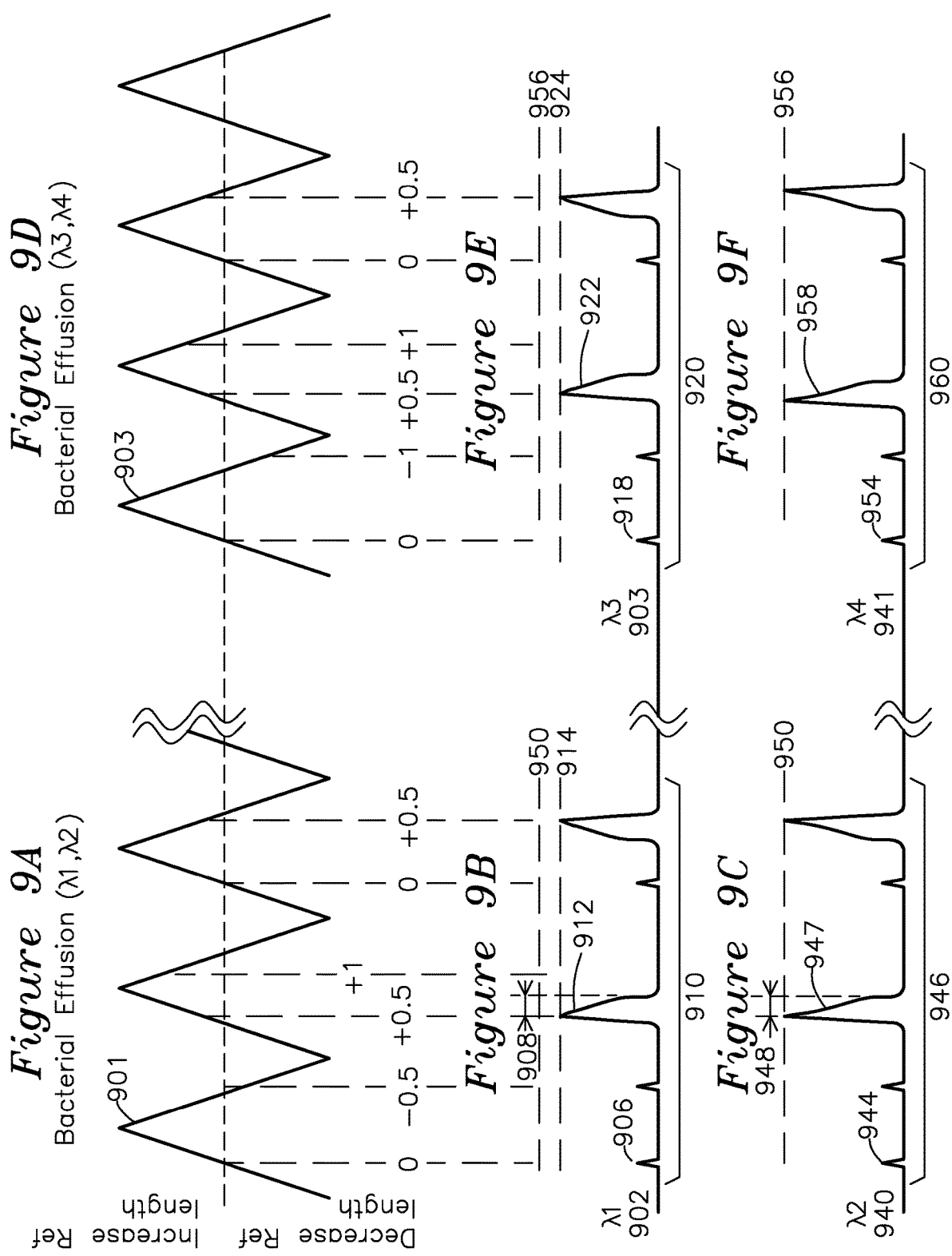

Optical Waveguide system for OCT measurement of TM

INFRARED OTOSCOPE FOR CHARACTERIZATION OF EFFUSION

CROSS-REFERENCE

This application is a continuation application of Ser. No. 15/609,015, filed May 31, 2017, which is incorporated herein by reference in its entirety.

FIELD OF THE INVENTION

The present invention relates to an otoscope for characterization of fluid in an ear. In particular, the invention relates to the detection of bacteria in a fluid opposite a membrane using a measurement of optical properties of the fluid and bacteria using one or more dual wavelength optical sources and a detector which is exclusively responsive to a particular source during a particular time interval.

BACKGROUND OF THE INVENTION

Acute Otitis Media (AOM) is a common disease of the inner ear, involving tissue inflammation and fluidic pressure which impinges on the tympanic membrane. Acute Otitis Media may be caused by a viral infection, which generally resolves without treatment, or it may be caused by a bacterial infection, which may progress and cause hearing loss or other deleterious and irreversible effects. Unfortunately, it is difficult to distinguish between viral or bacterial infection using currently available diagnostic devices, and the treatment methods for the two underlying infections are quite different. For bacterial infections, antibiotics are the treatment of choice, whereas for viral infections, the infection tends to self-resolve, and antibiotics are not only ineffective, but may result in an antibiotic resistance which would make them less effective in treating a subsequent bacterial infection. It is important to accurately diagnose acute otitis media, as AOM can be a precursor to chronic otitis media with effusion (COME), for which surgical drainage of the effusion and insertion of a tube in the tympanic membrane is indicated.

The definitive diagnostic tool for inner ear infections is myringotomy, an invasive procedure which involves incisions into the tympanic membrane, withdrawal of fluid, and examination of the effusion fluid under a microscope to identify the infectious agent in the effusion. Because of complications from this procedure, it is only used in severe cases. This presents a dilemma for medical practitioners, as the prescription of antibiotics for a viral infection is believed to be responsible for the evolution of antibiotic resistance in bacteria, which may result in more serious consequences later in life, and with no efficacious treatment outcome, as treatment of viral infectious agents with antibiotics is ineffective. An improved diagnostic tool for the diagnosis of acute otitis media is desired.

OBJECTS OF THE INVENTION

A first object of the invention is a device for measurement of infectious agents present in an individual suspected of suffering from acute otitis media, the device having a plurality of optical sources, each optical source operative at a unique wavelength or range of wavelengths, each optical source operative within a particular range of wavelengths for an interval of time which is exclusive from the interval of time when optical sources at other wavelengths are operative, the device having a detector for measurement of reflected optical energy, the detector measuring a ratio of detected optical energy at a first wavelength to detected optical energy at a second or third wavelength, thereafter forming a ratio metric value as a proxy for estimated bacterial load.

A second object of the invention is a method for determination of bacterial concentration by successively illuminating a first surface of a membrane using a first and second wavelength at exclusive time intervals, measuring the reflected optical energy from the opposite surface of the membrane during each associated interval, forming a ratio of the first wavelength and second wavelength detector responses from the associated illumination events, each illumination event at a unique wavelength or range of wavelengths, where at least one of the illumination wavelengths corresponds to a bacterial absorption band, and another of the illumination wavelengths is in a wavelength with non-absorption or non-scattering characteristic for a bacterial colony or group of dispersed bacterium.

A third object of the invention is a speculum tip for insertion into an ear canal, one or more pairs of optical sources, each optical source coupling an optical output through the speculum tip, each optical source operative in a unique wavelength or range of wavelengths, each pair of optical sources generating a first optical output at a first wavelength selected for reflective attenuation for either watery fluid or bacteria, and also generating a second wavelength selected for comparative non-attenuation reflection for either watery fluid or bacteria, the second wavelength operative near the first wavelength, where reflected optical energy from the tympanic membrane is directed to a detector responsive to each optical source wavelength for optical energy reflected into the speculum tip, the detector coupled to a controller measuring a ratio of detector response from said first and said second wavelength, thereby forming a metric indicating the presence of bacteria and/or watery fluid from the detector response ratio associated with each pair of emitters.

SUMMARY OF THE INVENTION

In a first example of the invention, a controller enables one of a first plurality of optical sources, or alternatively a single first optical source at a wavelength for bacterial absorption, and one of a second plurality of optical sources, or alternatively a second optical source operative at an adjacent wavelength which is non-absorptive for bacteria, an optional third source operative at a wavelength absorptive for watery fluid and an optional fourth source operative at an adjacent non-absorptive wavelength for watery fluid, each optical source or sources optionally operative at alternating or exclusive intervals of time. Each wavelength source is optically coupled through a tapered speculum which is inserted into the ear canal of a subject to be examined. The optical beam from each optical source may be carried as a directed beam, or the optical beam may be carried in an annular light guide or light pipe which surrounds the speculum, the optical energy from the illumination configuration impinging onto a front (distal) surface of a tympanic membrane, the tympanic membrane having a bacterial film or bacterial fluid on an opposite (proximal) surface of the tympanic membrane to be characterized. Reflected optical energy is coupled into the speculum tip to a single detector having a first wavelength response for energy reflected from the first source and a second wavelength response for energy reflected from the second wavelength source, or to separate detectors which are operative in each optical wavelength range of a respective optical source. The first wavelength response and second wavelength response are averaged over the associated interval the respective optical source is enabled to form an average measurement for each first wavelength response and each second wavelength response, and a ratio is formed from the two measurements. A first wavelength is in an absorption or scattering range of wavelengths for a bacterium to be characterized, and a second of the wavelengths is adjacent to the first wavelength and outside of the bacterial scattering or absorption wavelength. The response ratio for the first and second wavelength is applied to a polynomial or to a look-up table which provides an estimate of bacterial load from the ratio of power in the first wavelength to the power in the second wavelength, optionally compensating for the wavelength specific attenuation when absorptive or scattering fluid is not present, for example by using a stored wavelength scaling coefficient which compensates for scattering alone. A similar ratio for the detector responses associated with the third and fourth wavelength sources which are in adjacent absorptive and non-absorptive wavelengths, respectively, for water may be formed as well.

In a second example of the invention providing axial extent specificity over the region of measurement, the first and second wavelength sources are selected as adjacent wavelengths for absorption response and non-absorption response for bacteria, and also have a short coherence length, with the optical output of each source directed to the proximal surface of the tympanic membrane and middle ear to be characterized after splitting the optical energy into a measurement path and a reference path. The measurement path directs optical energy to the fluid to be characterized having a length equal to the reference path, the reflected optical energy from the measured path and reflected path are combined, thereby forming a coherent response over a narrow depth range, which is set to include the proximal surface of the tympanic membrane and middle ear region to be characterized. The first wavelength source and second wavelength source are enabled during exclusive intervals of time, and the combined measurement path and reference path optical energy directed to a detector response to the associated wavelengths. The first wavelength detector response and second wavelength detector response form a ratio which is used as a bacterial load metric, the ratio metric acting as a proxy for detection of the presence of bacteria. The third and fourth wavelengths are selected as in the first example to be adjacent but comparatively scattering and non-scattering for watery fluid, and used to form a second ratio which acts as a proxy for detection of watery fluid in the selected axial extent.

For the first or second example, by combining the second metric (presence of watery fluid) with the first metric (presence of bacteria), a more complete survey of the scope of acute otitis media may be determined.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 shows a block diagram of an OCT measurement system for dual wavelength measurements.

FIGS. 6A and 6B shows a block diagram for a multi-wavelength detector.

FIGS. 7A, 7B, 7C, 7D, 7E, and 7F show waveform plots for a normal tympanic membrane.

FIGS. 8A, 8B, 8C, 8D, 8E, and 8F show waveform plots for viral effusion in a tympanic membrane.

FIGS. 9A, 9B, 9C, 9D, 9E, and 9F show waveform plots for bacterial effusion in a tympanic membrane.

DETAILED DESCRIPTION OF THE INVENTION

Figure 1:
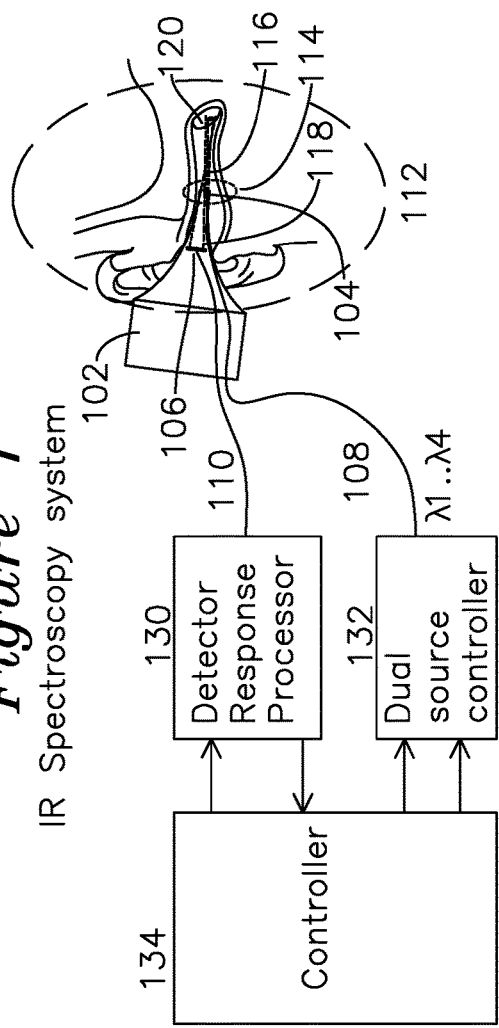
FIG. 1 shows a block diagram of an infrared spectroscopy system for making measurements of a tympanic membrane.
Figure 2:
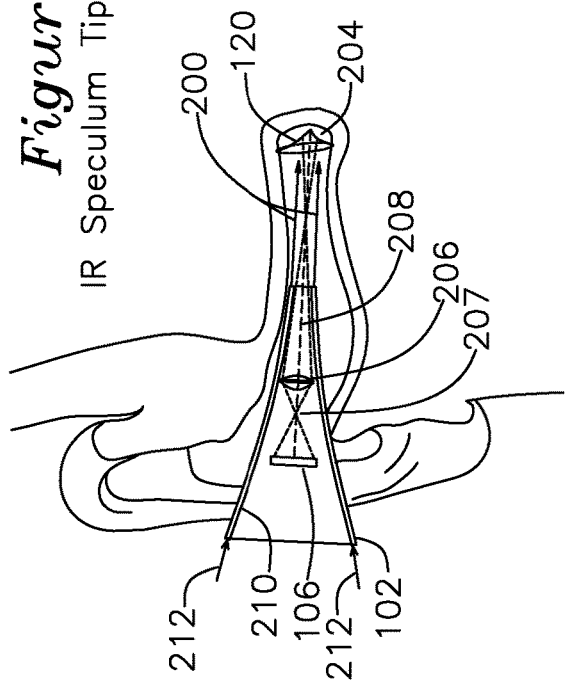
FIG. 2 shows a detail view of a speculum tip and optical components with respect to a tympanic membrane.

FIG. 1 shows a block diagram for an infrared (IR) spectroscopy system with an expanded view of the speculum tip in FIG. 2. A controller 134 is coupled to a detector response processor 130 and dual source controller 132. The dual source controller 132 enables and provides power to a first optical source (not shown) at a first wavelength $\lambda 1$ and a second wavelength source (not shown) at a second wavelength $\lambda 2$ during alternating intervals. The optical energy from the sources is directed through a speculum tip 102 and onto the front (distal) surface of a tympanic membrane 120 to be characterized, with the speculum tip 120 minimizing the reflected optical energy from inside the speculum tip 120 to the detector 106 through paths other than those which first reflect from the tympanic membrane 120. The reflected optical energy is sensed by an optical detector 106 and provided to image processor 130, which compares the reflected optical energy at a first wavelength to reflected optical energy at a second wavelength, and forms a metric such as ratio of reflected optical power measured at the detector in each wavelength $$\frac{\lambda 1_{refl}}{\lambda 2_{refl}}.$$

The wavelength metric may be used to estimate the likelihood of presence of bacteria or bacterial load in the inner ear fluid on the opposite (proximal) surface of the tympanic membrane 120.

FIG. 2 shows an example detailed view of IR speculum tip 102 with respect to other elements of an example embodiment. For bacterial measurement, first wavelength $\lambda 1$ and adjacent second wavelength $\lambda 2$ optical energy 212 may be coupled to the speculum tip 102 in any known manner which then couples to an annular light pipe, such as with a plurality of optical fibers positioned around the circumference of speculum tip 102, thereby coupling optical energy 200 to tympanic membrane 120 and to fluid 204 which may be on the proximal side of tympanic membrane 120, but without directly coupling to detector 106 until after reflection from tympanic membrane 120 and any fluid 204 which may lie opposite the tympanic membrane 120 distal surface which is facing the speculum tip 102. It may be additionally advantageous to add structure which exclude optical energy from sources other than tympanic membrane reflection. Reflected optical energy, which includes responses from tympanic membrane 120 and any fluid 204 which may be present, is focused by lens 206 into a dual range wavelength detector 106. In one example embodiment, the inner surfaces of speculum tip 212 are reflective and no lens or focusing mechanism 206 is present to guide unfocused reflected light to detector 106. Where a lens 206 is not present, the detector 106 is responsive to optical energy traveling directly from the tympanic membrane, as well as optical energy which has reflected from the inner reflective surface of the speculum tip 212. In this embodiment, identification of the selection region may be accomplished using a laser pointer (not shown) or other optical viewing system. The laser pointer emitter may optionally be disabled during measurement intervals to avoid contributing unwanted detector response from the laser pointer scattered reflection. A similar set of third and fourth wavelengths may be used to measure water content with adjacent wavelengths in absorption and non-absorption wavelengths. In another example embodiment, lens system 206 is present with the detector 106 having a small extent and comparatively small number of pixels and positioned at focal point 207, or alternatively it may be placed at an image plane as shown in FIG. 2 with a large number of pixels, such as 50×50 or 100×100, or a resolution which is governed by the pixel pitch and available inner diameter of speculum 102 at the image or focal plane.

Figure 3:
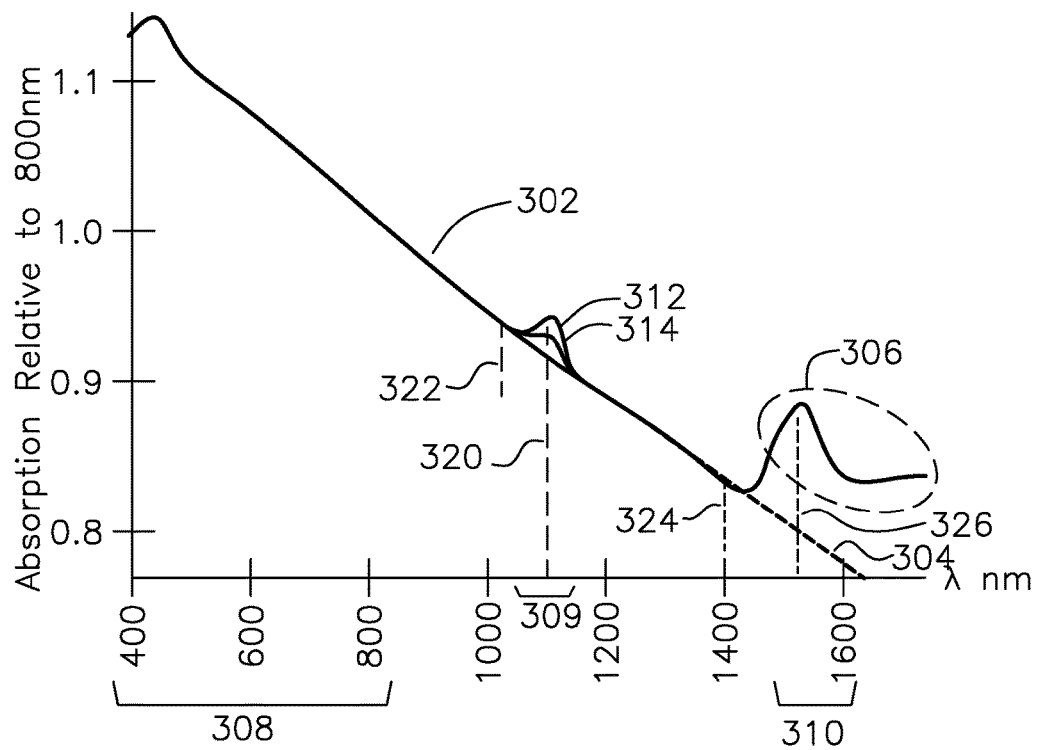
FIG. 3 shows a plot of scattered IR spectral response vs wavelength from a tympanic membrane.

FIG. 3 shows a spectral response for energy reflected from a tympanic membrane with and without bacterial/watery fluid. The reflection characteristic has a characteristic $$\frac{1}{f}$$

absorption falloff associated with Rayleigh scattering, whereby longer wavelengths have fewer scattering interactions and lower absorption than shorter wavelengths. The absorption plot 302 is generally reciprocal with increasing wavelength, however bacteria having a physical length which interacts with optical energy at an associated wavelength, such as the range 309 which has a greater absorption 312, 314 for various bacterium in region 309 of the plot for bacterial fluid compared to non-bacterial fluid in response plot 302. Particular bacteria which are absorptive in range 309 include *Haemophilus influenzae, Moraxella catarrhalis,* and *Streptococcus pneumoniae.* Similarly, an elevated absorption peak 306 is found associated with water absorption in a different range of wavelengths. In the present invention, the detector is responsive to reflected optical energy in a first wavelength range 309 such as 1050 nm to 1150 nm which provides for a decreased response at the detector due to bacterial scattering, and the detector uses absorption in an adjacent wavelength 322 such as 1000 nm or the visible optical range 308 of 400 to 800 nm, which may also be used as a fifth wavelength $\lambda 5$ for pointing and illuminating the region of examination used for forming the $\lambda 1$ and $\lambda 2$ or $\lambda 3$ and $\lambda 4$ metric ratios. In this case, $\lambda 5$ may be in a visible range or detection wavelength range for a 2D detector 106, with the $\lambda 5$ source having a narrow dispersion laser (not shown) for illuminating the region of examination and indicating a landmark region such as the "cone of light" of the tympanic membrane for locating the measurement region.

In an illustrative example, FIG. 3 326 shows a first wavelength with an increased absorption when bacteria is present (region 309) compared to second wavelength 322 which is unaffected by the presence of bacteria, and third wavelength 326 has greater absorption when watery fluid is present compared to fourth wavelength 324 which is adjacent to the absorptive wavelength for watery fluid. These examples are given for illustrative purposes, wavelengths for absorption by bacteria or water may vary from those shown in the example of FIG. 3. In the context of the present specification, wavelength specific absorption may also be referred to as scattering or reflective attenuation. In one example of the invention, a first wavelength operative for increased absorption or scattering in the presence of bacteria is in the range 1050 nm to 1150 nm, and an adjacent wavelength is one below 1050 nm or above 1150 nm. In another example of the invention, a third wavelength operative for increased absorption or scattering in the presence of watery fluid is the range 310 from 1450 nm to 1600 nm, and a fourth wavelength which is adjacent to the third wavelength is below 1450 nm or above 1600 nm.

Figure 4:
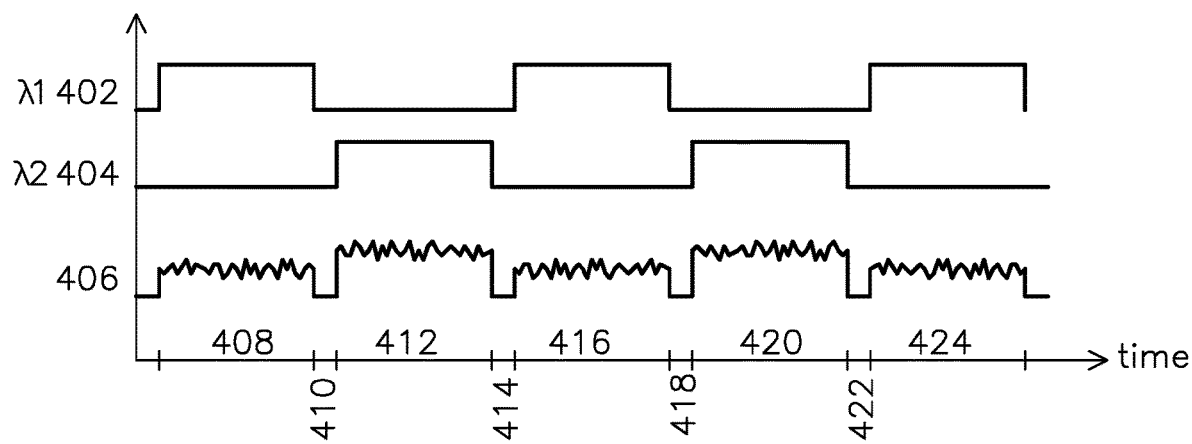
FIG. 4 shows a plot of waveforms for measurement of reflected optical energy from a first and second optical source.

FIG. 4 shows a plot of waveforms for operation of the device of FIGS. 1 and 2, which uses two optical sources such as $\lambda 1$ and $\lambda 2$, although the commutation (also known as time multiplexing) for four wavelengths may be done in any order. A first wavelength $\lambda 1$ optical source 402 is commutated on during intervals 408, 416, and 424 and off during exclusive intervals 412, 420 when the second wavelength $\lambda 2$ optical source is enabled. Intermediate gaps 410, 414, 418, 422 may be used for ambient light corrections at the detector, which may be used to estimate an ambient light and detector offset value, and thereafter subtracted from the detector response during intervals 408, 416, 424 of $\lambda 1$, and intervals 412 and 420 of $\lambda 2$. The detector response 406 includes detector noise, which may be averaged over the measurement interval 408, 416, 424 for the first wavelength or 412, 420 for the second wavelength $\lambda 2$. In one example of the invention extended from the one shown in FIG. 4, $\lambda 1$ is a wavelength of increased bacterial absorption, $\lambda 2$ is a nearby reference wavelength which is outside the bacterial absorption wavelength of $\lambda 1$, $\lambda 3$ is a wavelength for water absorption, $\lambda 4$ is a wavelength near to $\lambda 3$ but not affected by water absorption, and $\lambda 5$ is an optical wavelength for visualization, each wavelength $\lambda 1$ and $\lambda 2$ are commutated on during exclusive intervals as waveforms 402 and 404 of FIG. 4 for forming a bacterial metric $$\frac{\lambda 1_{refl}}{\lambda 2_{refl}},$$

optionally after which each wavelength $\lambda 3$ and $\lambda 4$ are commutated during exclusive intervals 402 and 404 to form fluid metric $$\frac{\lambda 3_{refl}}{\lambda 4_{refl}}.$$

Each corresponding metric may then be compared with a threshold for each metric to arrive at an estimated likelihood of presence of fluid or presence of bacteria. In one example of the invention, the respective bacterial or water fluid detector wavelength responses may be corrected for wavelength-specific attenuation or scattering (in the absence of watery fluid or bacteria) so that each pair of wavelengths (pathogen specific and adjacent) provide a unity metric ratio $$\left(\frac{\lambda 1_{refl}}{\lambda 2_{refl}} \text{ or } \frac{\lambda 3_{refl}}{\lambda 4_{refl}}\right)$$

when bacteria or watery fluid, respectively, are not present.

FIG. 5 shows a block diagram for an optical coherence tomography (OCT) characterization system, which has the benefit of narrow depth of axial specificity, which allows the response being measured to be restricted to a particular axial depth and range of depth, such as the proximal surface of the tympanic membrane and middle ear region. A low coherence source 514 having a plurality of wavelength range outputs includes a first wavelength λ1 and a second wavelength λ2 which are directed along path 518 to first splitter 516, and thereafter to second splitter 526. Half of the optical energy is thereafter directed to the measurement optical path 528, and half to mirror 512 and movable reflector 508, which adjusts the length of the reference path to be equal to the measurement path length which includes the proximal surface of the tympanic membrane and middle ear region. The optical energy returned from the reflector 508 and returned from tympanic membrane 532 combine at second splitter 526, and the summed optical energy continues to first splitter 516 and thereafter to mirror 524 and detector 520. Where the reference optical path (optical distance from splitter 526 to reflector 508) is exactly the same length as measurement optical path (from second splitter 526 to tympanic membrane 532), the coherently summed reference optical energy and reflected optical energy is directed, in sequence, to second splitter 526, first splitter 516, mirror 524, and to detector 520. The short coherence length of source 514 provides depth specificity, which allows measurement of bacterial response, typically with specificity of less than an optical wavelength in depth on the proximal side of tympanic membrane 532. Schematic FIG. 5 is shown for illustration only, other configurations of optical mirrors and splitters may be used.

FIG. 6A shows a first example of a multi-wavelength detector 520A, where a first wavelength λ1 detector 602 is responsive to λ1 and transparent for second wavelength λ2 associated with second detector 604. By bonding a first detector 602 and second detector 604 together using an optically transparent adhesive, the front-facing detector 602 is transparent for the optical energy λ2 of the detector 604 behind it. This construction of the detector 602/604 may require commutation of the various optical sources as was described in FIG. 4, particularly where one of the detectors has an out-of-band response to adjacent wavelength optical energy used for a different measurement, such as water vs bacterial absorption.

FIG. 6B shows another embodiment of a multi-wavelength detector 520A, which utilizes a diffraction grating 608 to separate the various wavelengths λ1, λ2, λ3, λ4, etc. to detector 606 for spatial isolation of each wavelength. Because the various wavelengths are spatially separated, this configuration of detector may permit the four optical sources to be operated continuously and simultaneously, as they are inherently non-interfering because of the spatial separation by wavelength not present in the detector configuration of FIG. 6A. Dark current detector response (the detector response in the absence of optical energy used to establish a baseline response level which is subtracted from a reading when optical energy is present) may be made before or after the optical sources are enabled.

FIGS. 7A, 7B, 7C, 7D, 7E, and 7F show associated waveforms for positional drive 701 and 703, which modulate the axial position of reflector 508 of FIG. 5, where the position "0" corresponds to position 536*b* of FIG. 5, the position "−0.5" indicates position 536*a*, "+0.5" indicates position 536*c*, and "+1.0" indicates position 536*d*.

For the attenuation plot of FIG. 3, and using λ1 at an exemplar maximum viral attenuation wavelength of 1100 nm and λ2 at an exemplar adjacent wavelength 1000 nm, and λ3 at an exemplar water absorption wavelength of 1500 nm and λ4 at an exemplar nearby wavelength of 1400 nm which is outside the water absorption wavelength, it is possible to compare the relative responses of λ1 with λ2, and λ3 with λ4 to determine the three conditions of clinical interest: absence of watery fluid, presence of effusion fluid without bacteria, and presence of effusion fluid with bacteria, as is desired for subjects suffering from ear discomfort. The apparatus and method thereby providing a diagnostic tool for viral vs bacterial infection, as well as determining that no fluid is present proximal to the tympanic membrane.

FIGS. 7A and 7D are plots of axial position for the reflector 508 of FIG. 5, FIGS. 7B and 7C show the λ1 and λ2 responses, respectively, which are differential for bacteria, and FIGS. 7E and 7F show the λ3 and λ4 responses, respectively, which are differential for presence of watery fluid. The waveforms 702, 740, 703, and 741 show equal amplitude detector responses 714 and 750 where no fluid is present proximal to the tympanic membrane. Responses 706, 744, 718, and 754 are minimal coherent reflections due to patches of ear wax, ear follicles, or other minor structures distal to the tympanic membrane, and responses 712, 713, 722, and 758 are the respective detector responses for λ1 through λ4, respectively at the tympanic membrane. The short duration of the responses 708, 748, 721, and 757 at position +0.5 near the tympanic membrane also indicates that only the tympanic membrane is providing return signal, and only over the short duration of coherent reflection from the tympanic membrane. As minimal differential attenuation is present which is specific to wavelength, the response amplitudes 714, 750, 724, and 756 are all equivalent amplitude.

FIGS. 8A and 8D similarly show a plot of reflector position 801 and 803, respectively, corresponding to the region of coherence about the tympanic membrane, as was described for FIGS. 7A and 7D. The plots of FIGS. 8B and 8C show the OCT responses from viral (watery) fluid proximal to the tympanic membrane. The responses 806, 844, 818, and 854 distal to the tympanic membrane are minimal, as before. The tympanic membrane responses and proximal responses 812, 841, 822, and 858 have an extended duration of response associated with the fluid boundary proximal to the tympanic membrane, and include a longer time extent 808 and 848 of response, related to the spatially expanded response from fluid adjacent to the tympanic membrane, compared to the narrow tympanic membrane detector response such as 712 of FIG. 7. The peak amplitude detector responses 814 (λ1) and 850 (λ2) are similar in amplitude, whereas the peak response 824 (λ3) is reduced compared to 856 (λ4) because of the differential absorption of water at λ3 compared to λ4.

FIGS. 9A and 9D show the reflector position plots with responses of FIGS. 9B, 9C, 9E, and 9F for bacterial effusion proximal to the tympanic membrane. The amplitude 914 of OCT detector response 912 to λ1 is reduced compared to the detector amplitude response 947 at λ2, which is not as absorptive for bacteria. The extent of OCT response 908 and 948 is lengthened, as before, due to the bacterial concentration which may be adjacent to the tympanic membrane. The water attenuation of λ3 compared to λ4 is shown in plots 903 and 941, with responses 922 attenuated at amplitude 924 compared to plot 958 at greater amplitude 956.

As described in the previous response plots, the ratio of reflected signal λ1/λ2 may be used to estimate bacterial concentration, and the ratio of reflected signal λ3/λ4 may be used to estimate fluid presence adjacent to the tympanic membrane, and the ratio may compensate for lower amplitude response from shorter wavelengths (having more Rayleigh scattering) of each pair of wavelengths such that the ratio is normalized to 1 for the absence of either bacteria or watery fluid in each respective ratio.

Figure 10:
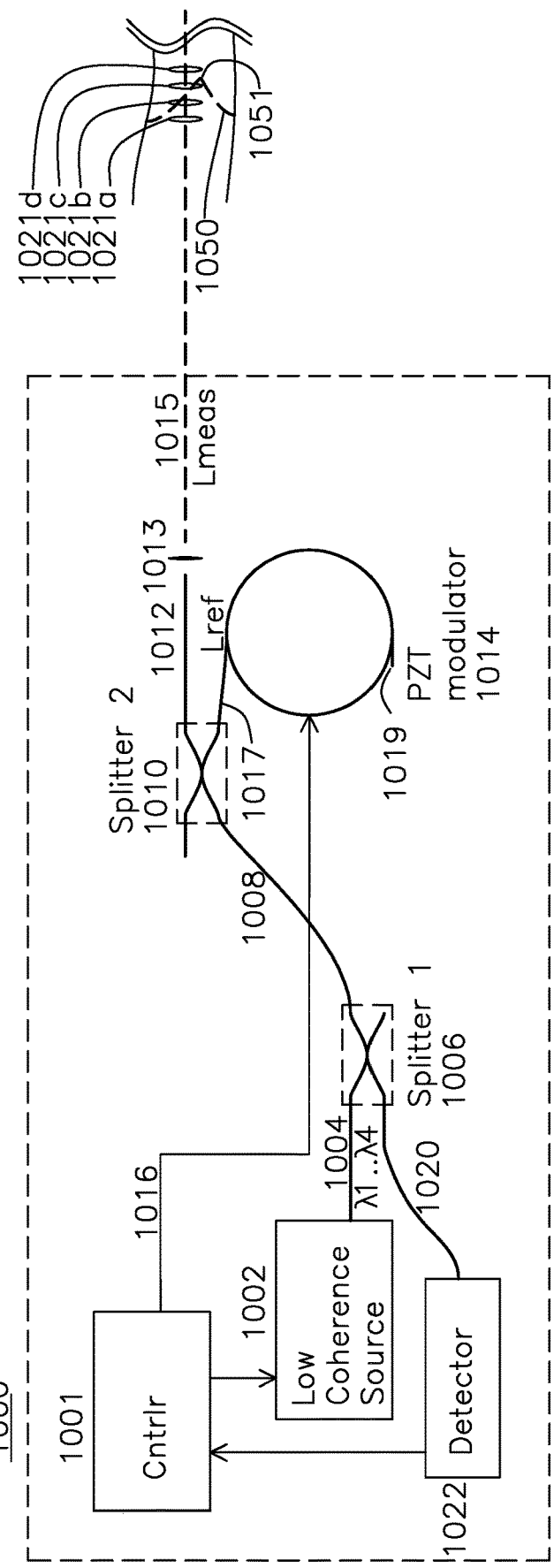
FIG. 10 shows a block diagram of an optical fiber based OCT system for dual wavelength in-fiber dual spectroscopy.

FIG. 10 shows a fiber optic architecture for performing OCT to form a differential measurements previously described. Low coherence source 1002 generates λ1, λ2, λ3, λ4 in a commutated sequence (for detector 1022 of FIG. 6A, or concurrently for the detector of FIG. 6B), which is applied to first splitter 1006, the low coherence source being coupled to optical fiber 1008 and to second splitter 1010, half of the optical source power directed thereafter to optical fiber 1012 and lens 1013, which directs the beam through the speculum tip (not shown), to tympanic membrane 1051, with reflections from the tympanic membrane and adjacent structures directed back along Lmeas path to lens 1013, optical fiber 1012, and back to second splitter 1010. The other half of the power traveling from the source 1002 through splitter 1004 to second splitter 1010 is directed to reference path 1017 with length Lref terminating in a polished fiber end 1019, which reflects optical energy in a counter-propagating direction and back to second splitter 1010. The reference path length Lref is equal to the total measurement length from second splitter 1010 to the tympanic membrane 1050. By adjusting Lref using the PZT modulator 1014 which changes the length of the optical fiber by stretching it longitudinally, the region of optical coherence can be modulated axially about the tympanic membrane.

The foregoing is a description of preferred embodiments of the invention. It is understood that various substitutions can be made without limitation to the scope of the invention. For example, other wavelengths may be preferable for bacterial absorption or water absorption than those specified.

What is claimed is:

1. A device for characterization of a liquid adjacent to a tympanic membrane, the device comprising:
    a low-coherence interferometer comprising at least one light source with an optical spectrum, wherein the optical spectrum comprises a first wavelength which is at least partially reflective from the tympanic membrane and at least partially absorptive by viral or bacterial effusion fluid and a second wavelength which is at least partially reflective from the tympanic membrane and less absorptive by the viral or bacterial effusion fluid than the first wavelength;
    a detector configured to receive reflected light from the tympanic membrane and to collect low-coherence interferometry data comprising a measurement of an optical power for at least the first wavelength and the second wavelength;
    a controller operably connected to the detector and configured to determine a membrane metric based at least on a ratio of the measurement of the optical power for the first wavelength and the second wavelength, and wherein the membrane metric indicates a presence of the viral or bacterial effusion fluid adjacent the tympanic membrane.

2. The device of claim 1, wherein the detector comprises a first detector responsive to the first wavelength and transparent to the second wavelength positioned in front of a second detector responsive to the second wavelength.

3. The device of claim 1, wherein the detector comprises a first detector adjacent to a second detector and a diffraction grating configured to direct the reflected light onto the first detector and the second detector.

4. The device of claim 1, wherein the first wavelength is in the range 1050 nm to 1150 nm and the second wavelength is below 1050 nm.

5. The device of claim 4, further comprising a second optical source in the visible regime aligned with at least a portion of the first wavelength and the second wavelength along an axis toward the tympanic membrane.

6. The device of claim 1, wherein the first wavelength and the second wavelength are measured at exclusive intervals of time.

7. The device of claim 1, wherein the first wavelength and the second wavelength are measured concurrently.

8. The device of claim 1, wherein one or more of the first wavelength or the second wavelength are selected to increase the ratio of the measurement of the optical power for the first wavelength and the second wavelength.

9. The device of claim 1, wherein the low coherence interferometer is a portion of an optical coherence tomography system.

10. The device of claim 1, wherein the membrane metric is applied to a look-up table to determine a bacterial or viral load.

11. The device of claim 1, wherein the membrane metric is determined based at least on the ratio of the measurement of the optical power for the first wavelength and the second wavelength as a function of depth of the measurement.

12. A method for characterizing a liquid adjacent to a tympanic membrane, the method comprising:
    directing light from a low-coherence interferometer comprising a light source, wherein the light comprises a first wavelength at least partially reflected by the tympanic membrane and absorbed by viral or bacterial effusion fluid and a second wavelength at least partially reflected by the tympanic membrane and less absorptive by the viral or bacterial effusion fluid than the first wavelength;
    measuring, at a detector, reflected light from the tympanic membrane, wherein the detector is configured to collect low-coherence interferometry data comprising a measurement of an optical power of the first wavelength and an optical power of the second wavelength;
    determining, at a controller operably connected to the detector, a ratio of the measurement of the optical power for the first wavelength and the second wavelength; and
    providing an indication of a presence of the viral or bacterial effusion fluid adjacent the tympanic membrane based on the ratio of the intensity of the first wavelength and the intensity of the second wavelength.

13. The method of claim 12, further comprising indicating a landmark region on the tympanic membrane using a second optical source.

14. The method of claim 12, wherein providing the indication of the presence of the viral or bacterial effusion fluid comprises comparing a membrane metric derived from the ratio to a look-up table and estimating a viral load or a bacterial load based on the comparison.

15. The method of claim 12, further comprising adjusting the first wavelength or the second wavelength to increase the ratio of the measurement of the optical power for the first wavelength or the second wavelength.

16. The method of claim 12, wherein the indication of the presence of the viral or the bacterial effusion fluid comprises an indication of acute otitis media or chronic otitis media with effusion.

17. The method of claim 12, further comprising adjusting a measurement path of the low-coherence interferometer relative to a reference path of the low-coherence interferometer and measuring a summed response from the measurement path and the reference path at the detector.

18. The method of claim 17, wherein the low-coherence interferometer comprises a portion of an optical coherence tomography system and wherein the providing the indication comprises restricting the ratio to a particular axial depth.

19. The method of claim 12, wherein the measuring further comprises measuring the reflected light as a function of depth and using a depth profile to provide the indication.

20. The method of claim 19, wherein providing the indication of the presence of the viral or bacterial effusion fluid further comprises using the depth profile and the ratio to distinguish a viral response from a bacterial response from a no effusion response.

21. The method of claim 12, further comprising directing light comprising a third wavelength and a fourth wavelength and forming a second ratio using the third wavelength and the fourth wavelength.

22. The method of claim 21, further comprising comparing the first ratio and the second ratio.

\* \* \* \* \*